(12) United States Patent
Rongeat et al.

(10) Patent No.: US 8,940,236 B2
(45) Date of Patent: Jan. 27, 2015

(54) DEVICE FOR INSPECTING A BIOLOGICAL FLUID

(75) Inventors: Nelly Rongeat, Grables (FR); Philippe Nerin, Montferrier sur Lez (FR); Patrick Brunel, Saint Aunes (FR)

(73) Assignees: Horiba ABX SAS, Montpellier (FR); Universite de Limoges, Limoges (FR); Centre National de la Recherche Scientifique CNRS, Paris (FR)

( * ) Notice: Subject to any disclaimer, the term of this patent is extended or adjusted under 35 U.S.C. 154(b) by 29 days.

(21) Appl. No.: 13/978,544

(22) PCT Filed: Jan. 2, 2012

(86) PCT No.: PCT/FR2012/000001
§ 371 (c)(1), (2), (4) Date: Aug. 15, 2013

(87) PCT Pub. No.: WO2012/093223
PCT Pub. Date: Jul. 12, 2012

(65) Prior Publication Data
US 2013/0316440 A1 Nov. 28, 2013

(30) Foreign Application Priority Data
Jan. 7, 2011 (FR) .................................. 11/00050

(51) Int. Cl.
*G01N 15/06* (2006.01)
*G01N 33/00* (2006.01)
(Continued)

(52) U.S. Cl.
CPC ........ *G01N 21/6486* (2013.01); *G01N 15/1031* (2013.01); *G01N 15/1427* (2013.01);
(Continued)

(58) Field of Classification Search
USPC ................. 422/50, 68.1, 82.01, 82.05, 82.07; 436/43
See application file for complete search history.

(56) References Cited

U.S. PATENT DOCUMENTS 5,351,118 A 9/1994 Spinell
5,675,517 A * 10/1997 Stokdijk ........................ 702/85
(Continued)

FOREIGN PATENT DOCUMENTS

DE 103 04 653 8/2004
FR 2 898 190 9/2007

OTHER PUBLICATIONS

International Search Report issued Mar. 29, 2012 in PCT/FR12/00001 Filed Jan. 2, 2012.

*Primary Examiner* — Brian J Sines
(74) *Attorney, Agent, or Firm* — Oblon, Spivak, McClelland, Maier & Neustadt, L.L.P.

(57) ABSTRACT

A device for inspecting a biological fluid, including a channel through which the fluid flows, a first inspection module arranged in a first region of the channel, and a second inspection module arranged in a second region of the channel, the device configured to provide a quantity that is representative of output of the second inspection module. The first inspection module is configured to measure at least one electrical property of the fluid passing through the first region. The second inspection module is configured to measure at least one optical property of the fluid passing through the second region. The inspection device also includes a controller connected to the first inspection module and to the second inspection module and configured to control the second inspection module according to the output of the first inspection module.

9 Claims, 7 Drawing Sheets

Figure 1:
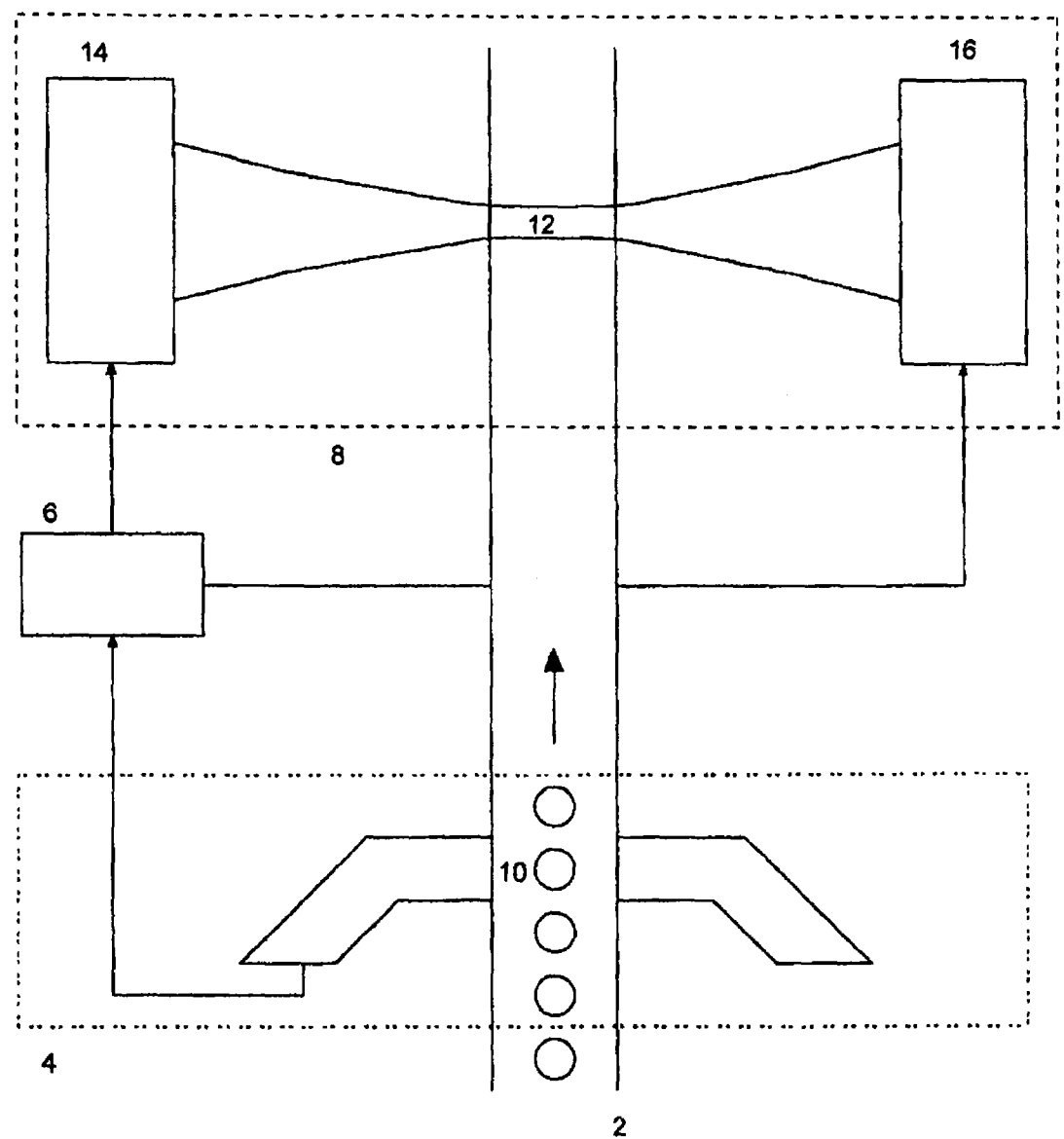

(51) Int. Cl.
*G01N 33/48* (2006.01)
*G01N 21/64* (2006.01)
*G01N 15/10* (2006.01)
*G01N 15/14* (2006.01)
*G02B 27/09* (2006.01)

(52) U.S. Cl.
CPC .... *G02B27/0927* (2013.01); *G01N 2015/1037* (2013.01); *G01N 2015/1477* (2013.01); *G01N 2015/1486* (2013.01)
USPC ............ 422/82.05; 422/50; 422/68.1; 436/43

(56) References Cited

U.S. PATENT DOCUMENTS

| | | | |
|---|---|---|---|
| 6,211,956 B1* | 4/2001 | Nicoli | 356/337 |
| 6,678,040 B1* | 1/2004 | Suzuki | 356/39 |
| 6,800,251 B2* | 10/2004 | Catterall et al. | 422/537 |
| 6,816,257 B2* | 11/2004 | Goix | 356/318 |
| 7,016,523 B1 | 3/2006 | Ogawa | |
| 7,328,889 B2* | 2/2008 | Mototsu | 267/140.13 |
| 7,510,685 B2* | 3/2009 | Muller et al. | 422/514 |
| 8,158,439 B2* | 4/2012 | Shibata | 436/179 |
| 2004/0072278 A1 | 4/2004 | Chou et al. | |
| 2004/0224380 A1 | 11/2004 | Chou et al. | |
| 2009/0059207 A1 | 3/2009 | Nerin et al. | |

* cited by examiner

DEVICE FOR INSPECTING A BIOLOGICAL FLUID

The invention relates to a device for inspecting a biological fluid, especially for flow cytometry and haematology.

The field of cytological analysis has undergone considerable expansion with the development of modern optics.

The integration of polychromatic sources has made it possible to produce analysers that are capable of detecting and analysing several types of cells, and progress in physics has enabled the quality of the measurements to be improved.

However, such progress has reached its limits. There are, in fact, several ways of producing a polychromatic source in order to integrate it into an analyser, but they all have disadvantages which limit modern analyses.

A first way consists in using sources of the QTH (quartz tungsten halogen) lamp type or of the discharge source type, for example a mercury lamp or a xenon lamp.

QTH lamps have relatively low brightness. Application of the laws of thermodynamics to the tungsten filament brought to the temperature (T) of emissivity $\epsilon(T)$ shows that the brightness is low whatever the wavelength.

In addition, an increase in power can be achieved only at the expense of the lifetime, because only a significant increase in the temperature of the filament causes an increase in the photon flux. However, a large increase in the temperature of the tungsten filament beyond 3000° C. causes non-reversible ageing mechanisms which limit the lifetime to less than 1000 hours.

Furthermore, the power density at the point of measurement can be increased only by choosing a shaping optics that has a large numerical aperture. In practice, the incident illumination cone is open to more than 30 degrees. This limits the possibilities of measuring light diffracted at small angles, as is conventionally carried out in flow cytometry systems.

Although the brightness of a discharge source can be increased considerably as compared with a QTH lamp, a number of disadvantages must, however, be noted:

they are extended sources, with low spatial coherence, which are therefore unsuitable for the measurement of small-angle diffraction signals,
  these sources are pulsed with the aid of very high voltages and therefore cause electromagnetic interference in the electronic components for processing the low-level signals,
  such interference, which is pulses the frequency spectrum of which is very widespread, are therefore very difficult to filter out and interfere directly with the signals measured by the flow cytometry system, since it is based in principle on the generation and processing of pulses,
  they have extreme mechanical fragility, and
  their lifetime does not exceed some 100 hours of use in a flow cytometry system intended for intensive use.

To summarise, those types of source have limited lifetimes and exhibit a spectral power density that is too limited for applications in cytometry and for their use within the field of fluorescence. In addition, those extended sources with low spatial coherence are unsuitable for small-angle diffraction measurements.

Another approach has been to use lasers, which have more valuable energy properties. However, the lasers used are monochromatic, which requires the joint use of a plurality of aligned lasers in order to carry out successive or simultaneous measurements.

That approach presents consequent problems in producing the analyser in terms of alignment, and gives rise to high production costs.

Similar problems also arise within the context of light sources having a spectrum that is not very extended.

The invention is going to improve the situation.

To that end, the invention proposes a device for inspecting a biological fluid, comprising a channel through which the fluid flows, a first inspection module arranged in a first region of said channel, and a second inspection module arranged in a second region of said channel, the device being arranged to provide a quantity that is representative of the output of the second inspection module.

The first inspection module is arranged to measure at least one electrical property of the fluid passing through the first region. The second inspection module is arranged to measure at least one optical property of the fluid passing through the second region.

The inspection device further comprises a controller, which is connected to the first inspection module and to the second inspection module and is arranged to control the second inspection module according to the output of the first inspection module.

The device of the invention is particularly advantageous because it allows the optical measurement and the initial electrical measurement to be linked in a controlled manner. Thus, it becomes possible to use a plurality of light sources, such as, for example, monochromatic lasers, a white laser, also called a supercontinuum laser, or an LED, or an RCLED with a reduced implementation cost and improved mechanical and optical stability.

Figure 2:
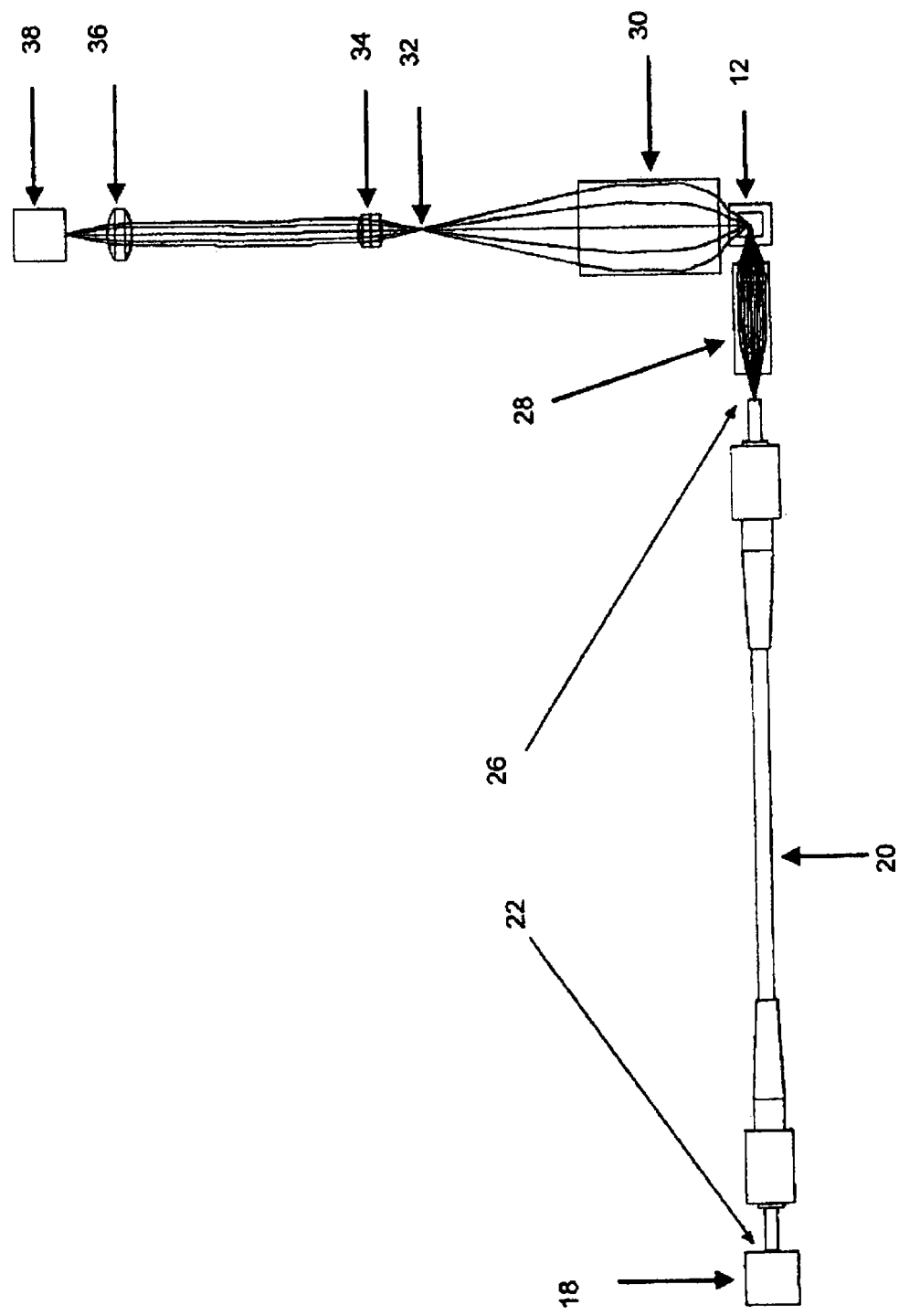
Figure 3:
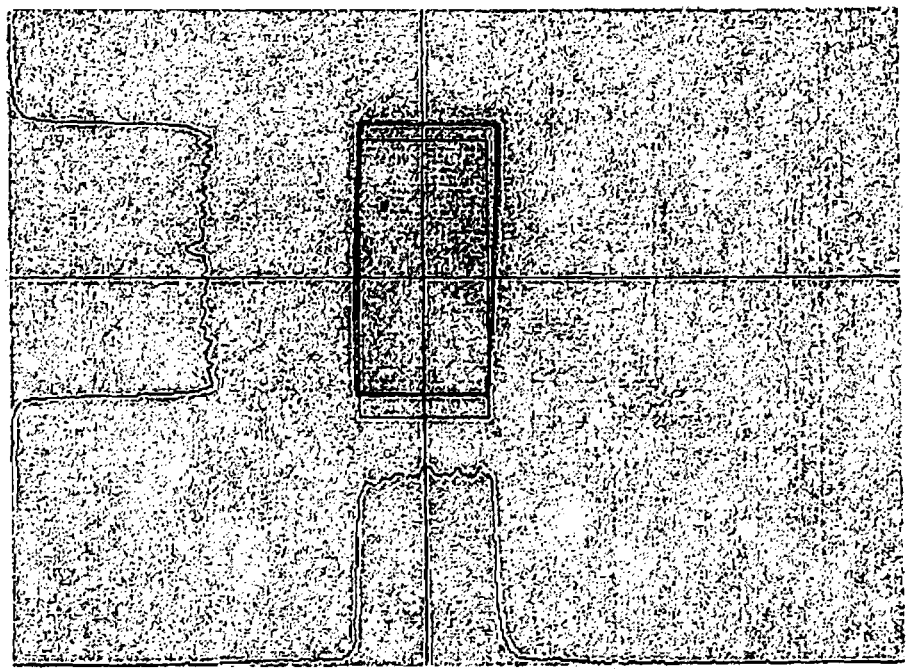
Figure 4:
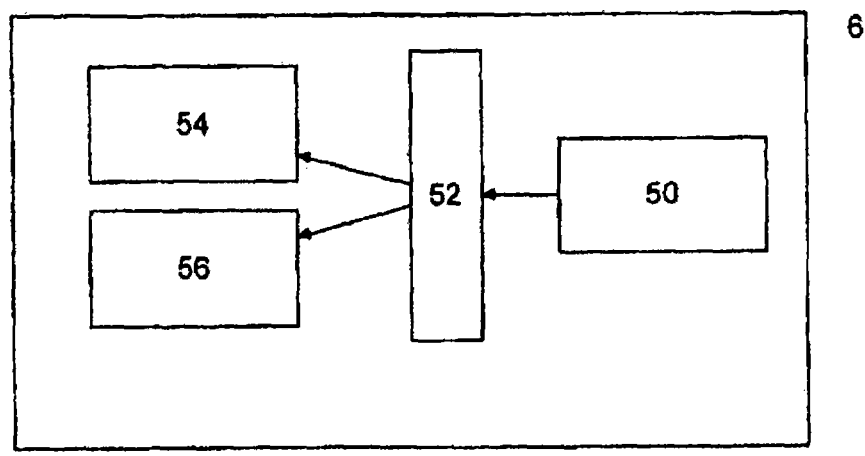
Figure 5:
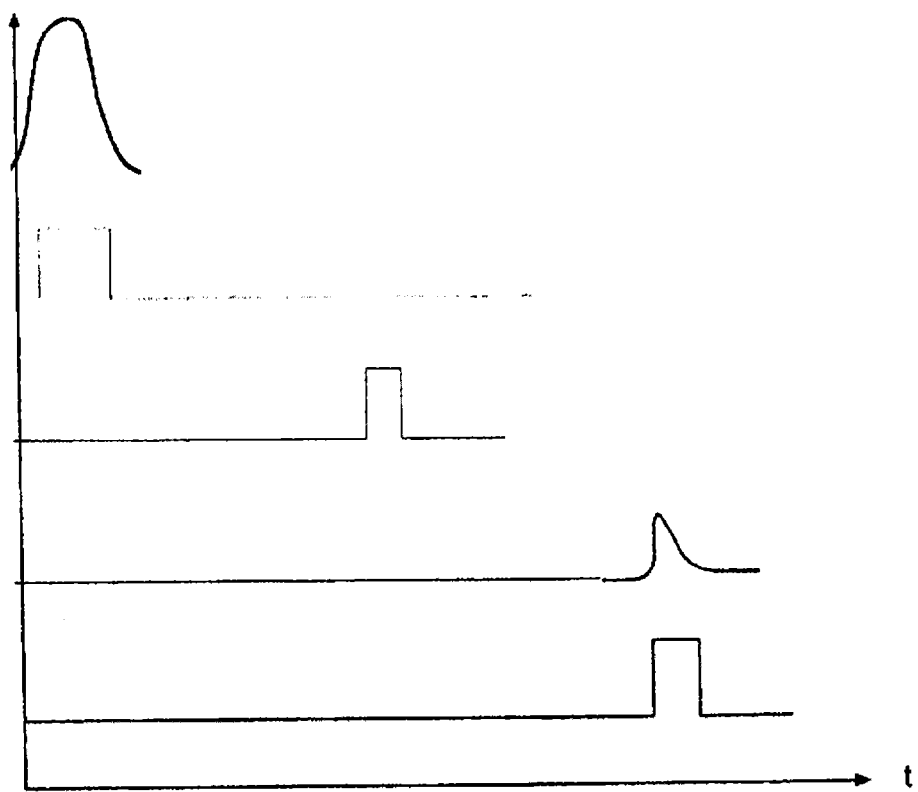
Figure 6:
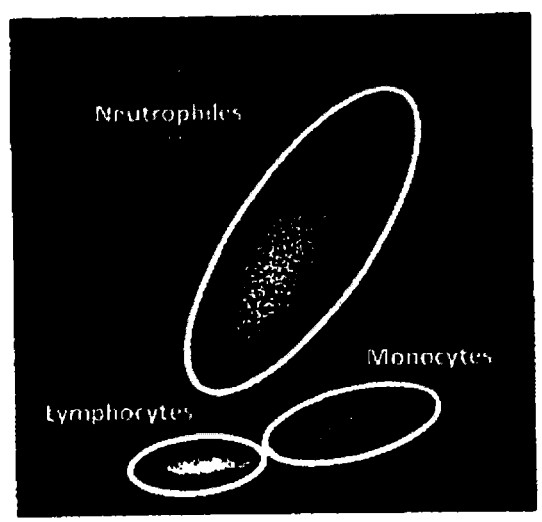
Figure 7:
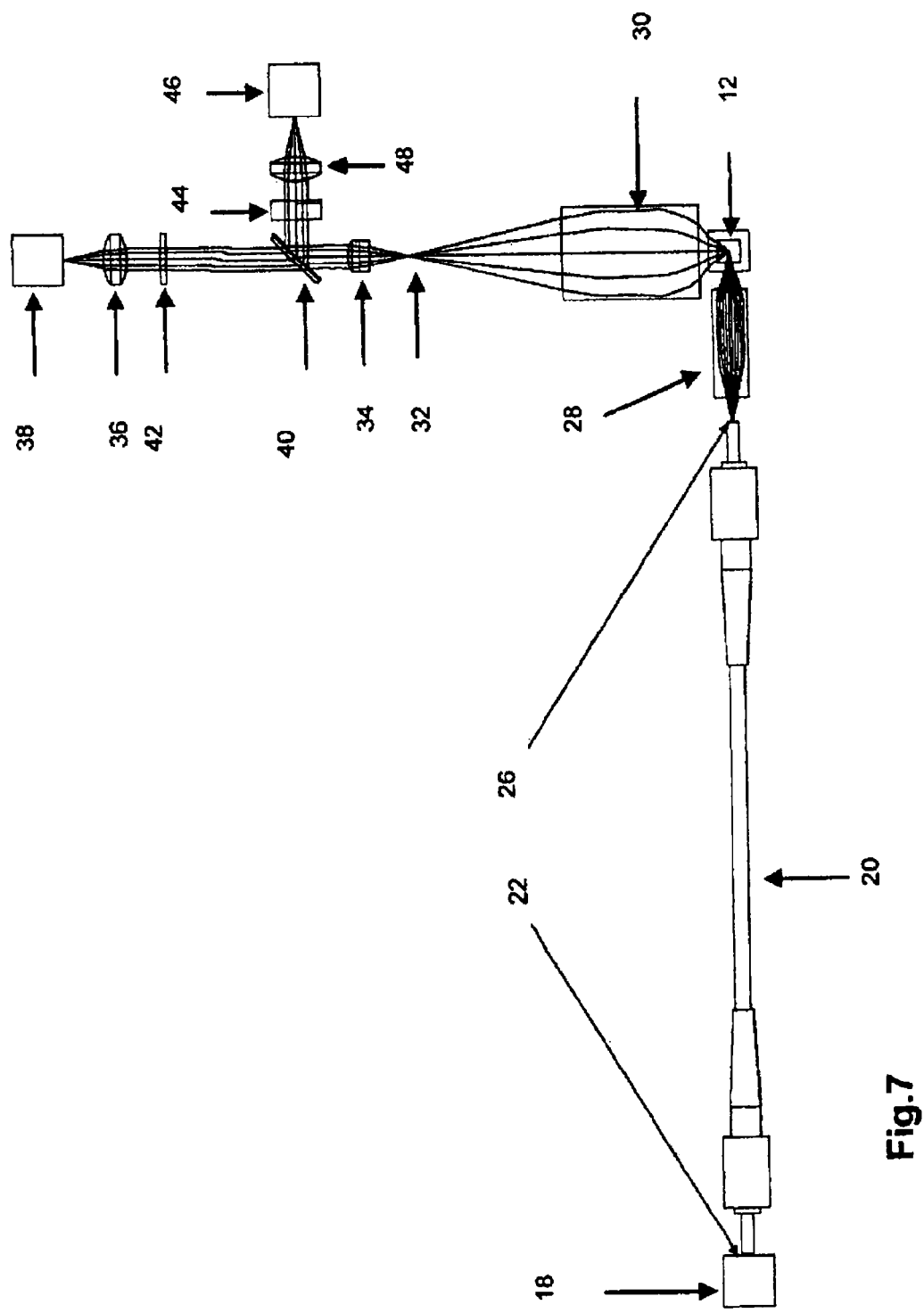
Figure 8:
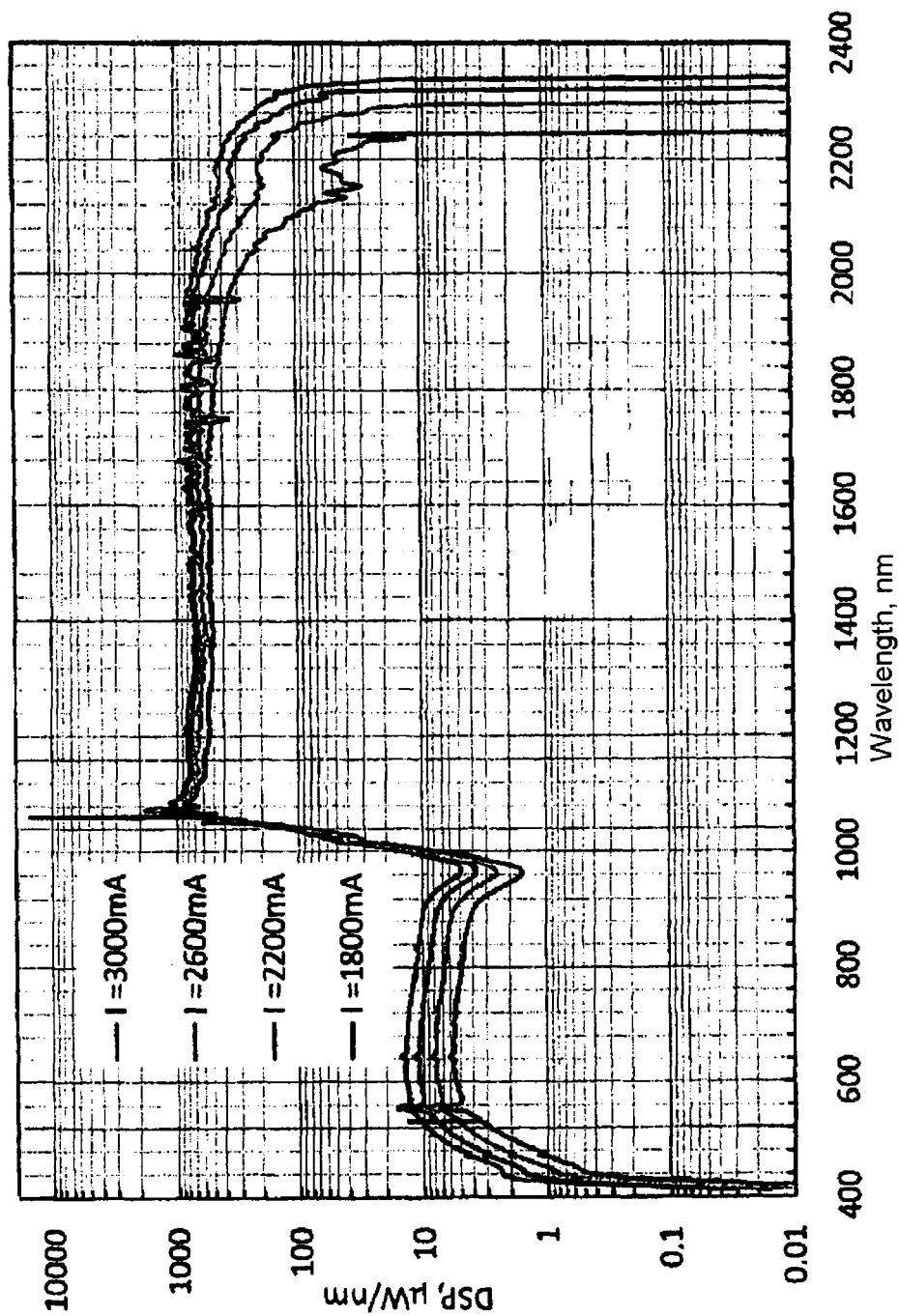

Other features and advantages of the invention will better become apparent upon reading the following description, which is taken from examples which are given by way of illustration and without implying any limitation and are taken from the drawings, in which:

FIG. 1 shows a schematic diagram of part of a device according to the invention, FIG. 2 shows a first embodiment of the second inspection module of FIG. 1, FIG. 3 shows an image of the optical window resulting from the illumination unit of FIG. 2, FIG. 4 shows a schematic diagram of the controller of FIG. 1, FIG. 5 shows the various signals in the device of FIG. 1 as a function of time, FIG. 6 shows an example of an image obtained with the device comprising the illumination module of FIG. 2, FIG. 7 shows a second embodiment of the second inspection module of FIG. 1, FIG. 8 shows a luminous spectrum of the illumination source of FIG. 7, and FIGS. 9 to 11 show examples of images obtained with the device comprising the illumination module of FIG. 7.

The drawings and description below contain, for the most part, elements of a specific nature. They may therefore not only serve the purpose of better understanding of the invention but also contribute to the definition thereof, where appropriate.

FIG. 1 shows an inspection device according to the invention, which comprises a fluid channel 2, a first inspection module 4, a controller 6, and a second inspection module 8.

In the example described here, the fluid that is being analysed is blood, which flows through the channel 2 in the direction indicated by an arrow in FIG. 1. Although the invention can be used particularly advantageously in the field of haematological counting, it relates more generally to any type of fluid and to any type of biological analysis. It may thus be used for carrying out flow cytometry or the like.

The channel 2 is part of the measuring vessel of the device. As is already known, for example from patent FR 2 878 032, the measuring vessel comprises a focusing nozzle and a capillary arranged opposite the end thereof.

This form allows an effect of hydrodynamic shielding to be obtained, the cells of the blood entering a zone or region, called the measuring zone or region, one by one. FIG. 1, with the channel 2, is a close-up view of the device in the region of the measuring zone.

Although the invention is described with reference to cells, it must be understood that it is suitable for the inspection of a fluid in order to detect more generally particles therein. A particle is to be understood in a non-limiting manner as being cells, vesicles, parasites, or viruses.

In the example described here, the channel 2 comprises a first region or zone 10 and a second zone or region 12, which are separated by an axial distance of 210 μm. That distance can vary according to the devices and generally remains between several tens of micrometers and several hundred micrometers. Since they are at the same level, it is possible to speak either of the distance between the inspection modules or of the distance between the regions.

In the following, the terms zone and region may be used and denote the same element, that is to say a delimited portion of the channel 2 through which the cells of the blood to be analysed will pass one by one.

The first inspection module 4 is arranged in the first region 10 and allows an electrical or magnetic property of the fluid passing through that region to be measured.

In the example described here, that measurement is carried out through a micro-orifice situated in the channel 2. The first inspection module 4 comprises a source of current which is connected to the micro-orifice, so that an electric current passes through the channel 2 in the region thereof.

In the absence of a cell, the fluid passing through the first region 10 defines a load impedance Z, which is measured by two electrodes located on either side of the micro-orifice. When a cell of the blood passes through the first region 10, it causes an increase in the impedance Z. This variation in the impedance on the one hand allows the volume of the cell to be determined and on the other hand enables a cell count to be carried out.

The second inspection module 8 is arranged in the second region 12 and allows an optical property of the fluid passing through that region to be measured.

The second module 8 comprises on the one hand an illumination unit 14 and on the other hand an analysis unit 16. Those elements will be described below with reference to FIGS. 2 and 7.

FIG. 2 shows a first embodiment of the second inspection module 8, observed in the axis of the channel 2.

In this embodiment, the illumination unit 14 comprises an illumination source 18 which comprises a resonant-cavity light-emitting diode (RCLED), such as a ZL60003 from Zarlink, and a light guide 20. The illumination source 18 is connected to an input end 22 of the light guide 20.

As has been described in document FR 2 878 032, the light guide 20 comprises an output end 26, opposite which a shaping system 28 is arranged.

The end portion of that optical fibre forms the end 26 and has been treated differently, by micro-machining, so as to obtain a beam profile such as that shown in FIG. 3 in the second region 12. In a variant, it would be possible to use a microstructured optical fibre, a conventional guided optical fibre, or other optical systems such as a catadioptric, refractive or diffractive system. The optical system may also be anamorphic.

On the other side of the channel 2, the analysis unit 16 comprises an objective 30, a diaphragm 32 and collimating lenses 34 followed by a focusing lens 36 on the optical analyser 38.

The optical analyser 38 is known per se and can comprise a detector which can be a photomultiplier or a photodiode or any other photoelectric detection device.

The analysis unit 16 can be adjusted so that the light signal that is collected corresponds to (an) expected effect(s) of interaction of the light with the fluid under examination: small-angle diffraction and/or large-angle diffraction and/or absorption and/or fluorescence and/or fluorescence lifetime.

In the example described here, the illumination source 18 formed by the RCLED has a very rapid response time, approximately 3 ns. The luminous spectrum observed at the output of that optical component extends from 640 to 660 nm.

The illumination source 18 formed by the RCLED also has the advantage that it can be Q-switched, that is to say it emits its light radiation on command.

The command is produced by the controller 6. As is shown in FIG. 4, the controller 6 comprises a computer 50, a limiter 52, and two signal generators 54 and 56.

As is apparent from FIG. 1, the controller 6 is connected on the one hand to the first inspection module 4 and on the other hand to the second inspection module 8. The role of the controller 6 is to control the activation of the second inspection module 8 when a cell has been detected by the first inspection module 4.

To that end, the controller 6 receives the detection signal from the first inspection module 4 and transmits a control signal for activation of the second inspection module 8 with a delay that allows a group of variables to be taken into account, which group of variables can be the following quadruplet:

the distance between the measuring zone of the first inspection module 4 and the measuring zone of the second inspection module 8,
the speed of the fluid in the channel 2,
the Q-switching time of the illumination source 18, which time may be equal to zero, and
the variation in the appearance of the cells.

Accordingly, in the inspection module 8, the illumination source 18 is Q-switched precisely at the time when a cell previously detected by the first inspection module 4 passes into the second region 12. Likewise, the optical analyser 38 is controlled to carry out the measurement precisely at the time when the illumination source 18 has been Q-switched.

The illumination source 18 is therefore illuminated just in time, as is the optical analyser 38, which limits the influence of any parasitic light to the greatest possible extent.

The data relating to the calculations of the appropriate delay can be stored in a memory and then processed by the computer 50 in order finally to be used for the Q-switching of the illumination source 18 or of the detection module 38. The data relating to the calculations of the appropriate delay can likewise be processed by the computer 50 and used for the Q-switching of the illumination source 18 or of the detection module 38 in real time.

The controller 6 can be in various forms, especially in the form of an electronic circuit comprising different types of electronic components, or electronic systems of the FPGA (field programmable gate array) or CPLD (complex programmable logical device) type.

The computer 50 can be in the form of a "look-up table", which will search for the value for the delay as a function of the quadruplet of variables described above as an example, or will employ a mathematical function which calculates the delay directly as a function of the quadruplet of variables.

At the output, the computer 50 controls the signal generators 54 and 56, one of which is connected to the illumination unit 14 and the other to the analysis unit 16.

The signal generator 54 generates a signal, the shape of which depends on the illumination source 18. In the example described here, the RCLED of the illumination source 18 is excited by a crenellated current signal, but the shape, the duration and the intensity of the pulse may vary as a function of the light source.

The signal generator 56 generates a measurement window which depends on the time width of the optical signal emitted by the illumination source 18, that is to say its duration, as well as on variations of that source or of the width of the signal 54. Accordingly, if the Q-switching time of the illumination source 18 can vary by a given quantity around its nominal value, the signal generator 56 generates a wider measurement window, which takes account thereof. By way of example, if the time width of the optical signal is 5 μs and the Q-switching time of the illumination source 18 varies by 3 μs relative to the average Q-switching time, the measurement window generated will be 8 μs.

The limiter 52 is a type of control barrier arranged between the computer 50 and the signal generator 54.

In current haematology analysers, the frequency of recurrence of maximum illumination calculated to measure the majority of leukocyte cells is approximately 10 kHz. Consequently, it is neither useful nor necessary for the generator 54 to excite the illumination source 58 with a frequency greater than that maximum frequency.

However, it is possible for the inspection module 4 to detect cells with a frequency greater than 10 kHz, and for the controller 6 consequently to be led to excite the illumination source 18 with too high a frequency. The limiter 52 makes it possible to avoid such situations.

The limiter 52 also makes it possible to avoid generating excitation signals for illumination sources that are limited in terms of frequency. That is the case, for example, for the illumination source of FIG. 7, which will be described below.

In the example described here, the limiter 52 is also connected to the signal generator 56, because it is of no use to generate a measurement window in the analysis unit if the illumination unit 18 is not activated, which would cause photonic noise.

The width of the pulse of the generator 54 is generally smaller than the width of the measurement window. However, the pulse width may also depend solely on the intrinsic properties of the source and on the speed of passage of the biological cells.

In a variant, the limiter 52 can be integrated individually into the signal generator 54 and/or into the signal generator 56 and/or into the computer 50. In another variant, the computer 50 can take account of the detection frequency of the cells in the calculation of the delay. The Q-switching time of the illumination source 18 may in fact vary as a function of the frequency of the Q-switching pulses that it receives. In another variant, the controller 6 may be provided with a memory for storing any useful parameter.

In other embodiments, the controller 6 can also send analysis parameters to the illumination unit 14 and/or to the analysis unit 16, in order to make specific adjustments as a function of the measurements carried out by the first inspection module 4.

FIG. 5 shows an example showing the various signals circulating in the device as a function of time in order to permit better understanding of the processing carried out by the controller 6:

the first curve represents the signal at the output of the first inspection module 4, the second curve represents the shaping of the signal of the first curve by the controller 6, the third curve represents the signal at the output of the controller 6, offset in time by a duration equal to t(delay) defined below, the fourth curve represents the (light) signal at the output of the illumination source 18, Q-switched with a delay the duration of which depends on the illumination source itself and which is t(Q-switching source), it being possible for that time to be zero according to the illumination source, and the fifth curve represents the control signal sent by the controller 6 to the analysis unit 16, called the measurement window above.

Accordingly, it is clear that the delay applied by the controller 6 is as follows: t(delay)=t(distance between modules)-t(Q-switching source). And the analysis unit 16 is controlled to measure in a time window comprising the duration of the pulse of the light source 18, called the measurement window above.

In a variant, the delay may also be calculated to take into account of the time for calculating and generating the control signal by the controller 6. The adjustment of that parameter may be manual or automatic.

The use of the controller 6 as a variable-delay control is very important and advantageous. It is in fact possible to use a controller 6 with a non-variable delay and to displace the relative positions of the first inspection module 4 and of the second inspection module 8. However, this type of arrangement requires adjustments that are complex and lengthy to implement.

In addition, it is also advantageous that the distance between the first inspection module 4 and the second inspection module 8 is neither too large nor too small, in order to avoid light reflections on the mechanical parts of the first region and to remain in the optimum conditions of hydrofocalisation.

Those constraints render the industrialisation of fixed-delay solutions very complex and expensive, which is not satisfactory.

The use of the controller 6 allows those problems to be solved, since it is very advantageous to adjust the calculation of the delay rather than to displace and realign the inspection modules. Furthermore, control of the illumination unit 14 and of the analysis unit 16 by the controller 6 enables the parasitic light to be limited by Q-switching the light pulse only at the moment when a cell passes and adjusting the measurement window to that pulse.

FIG. 6 shows an example of a matrix obtained by means of the device of FIG. 1 employing the second inspection module of FIG. 2.

Here, the inspection device constitutes a cell diagnostic analyser comprising two sequential measurements in the flow of particles. The first measurement corresponds to the electrical detection of the particles and the second measurement corresponds to the interaction between the light beam of the non-filtered RCLED and the particles.

As has been seen above, the RCLED is a Q-switched illumination source which is controlled by the controller by injection of a square signal with suitable tension values. As has been seen above, the RCLED has a very rapid response time (3 ns) and the light spectrum observed at the output of that optical component extends from 640 to 660 nm.

FIG. 7 shows a second embodiment of the inspection module 8, very similar to that of FIG. 2. It differs in that the illumination unit 14 (shown in FIG. 1) is modified, and in that the analysis unit 16 (shown in FIG. 1) further comprises a dichroic filter 40, wavelength filters 42 and 44 (FITC-3540B Exciter and FF01 530/43 from Semrock), as well as an additional optical analyser 46 with its focusing lens 48.

In this embodiment, the illumination unit 14 comprises an illumination source 18 which comprises a white laser instead of an RCLED. The white laser 18 is connected to an input end 22 of the light guide 20 by a photonic crystal optical fibre (not shown).

As has been described above, the light guide 20 comprises an output end 26, opposite which a shaping system 28 is arranged. The end portion of the optical fibre forms the end 26 and has been treated differently, by micro-machining, so as to obtain a beam profile such as that shown in FIG. 3 in the second region 12. As an alternative, it would be possible to use a microstructured optical fibre, a conventional guided optical fibre, or other optical systems such as a lens system.

The use of a white laser as the illumination source 18 opens up numerous possibilities.

In the example described here, the white laser 18 is obtained by coupling a pump laser having a maximum repetition frequency of 2 kHz, a light pulse width of 450 ps and a maximum pulse energy of 8 µJ to a highly non-linear photonic crystal optical fibre.

At the output of that fibre, the light spectrum observed extends from 380 nm to 1750 nm and forms an energy supercontinuum. An example of this supercontinuum spectrum is shown in FIG. 8. The white laser has an average power over the whole spectrum of 6 mW, for a maximum frequency of 2 kHz.

Figures 9, 10:
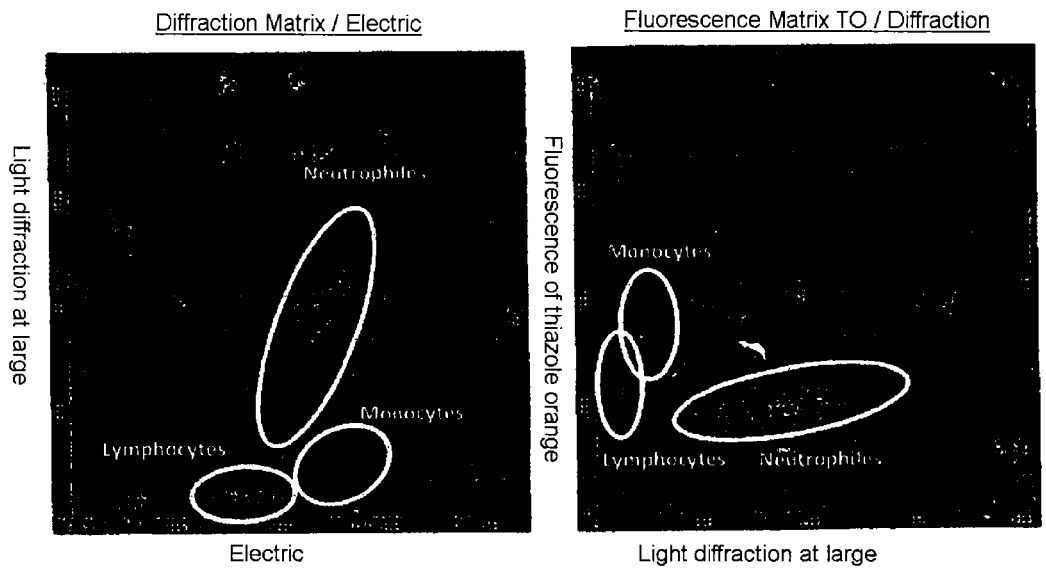

The use of a band-pass filter centred on the wavelength of 488 nm (FITC-3540B Exciter from Semrock) of bandwidth 36 nm allows Thiazole Orange to be excited. Accordingly, the average power of the light beam in this wavelength band is 290 µW, namely a peak power of 320 W. The light energy is here estimated at 145 nJ, which permits the measurement of fluorescence and diffraction signals with satisfactory signal-to-noise ratios, as is shown in FIG. 10.

The use of a white laser makes it possible to have a broad wavelength spectrum and to be able to filter the desired wavelengths as a function of the fluorochromes that are to be detected. The fluorochromes can in fact be excited only at specific wavelengths. The freedom of choice of fluorochromes that may be excited according to the expected result is therefore greater as a result of this broad-spectrum source. The illumination source 18 formed by the white laser also has the advantage of being Q-switched, that is to say it emits its light radiation on command.

The white laser of the illumination source 18 is a Q-switched laser which can be controlled by the controller 6 by injection of a square signal with suitable tension values. As has been seen above, the pump laser is a laser which emits in the infra-red range, with an emission wavelength of 1064 nm, and the maximum frequency of which is 2 kHz. The white laser is obtained by coupling that pump to a photonic crystal fibre.

The limiter 52 can be used particularly advantageously in this embodiment. It has in fact just been shown that the illumination source 18 of this embodiment has a maximum frequency of 2 kHz. Consequently, it is not necessary for the signal generator 54 to excite that source with a frequency greater than 2 kHz.

However, it is possible for the inspection module 4 to detect cells with a frequency greater than 2 kHz, and for the controller 6 consequently to be led to excite the illumination source 18 with too high a frequency. The limiter 52 makes it possible to avoid such situations. In the example described here, the limiter 52 separates a cell detection that is too close to the preceding one, so that the rate of the successive excitations of the illumination source remains equal to not more than 2 kHz.

Figure 11:
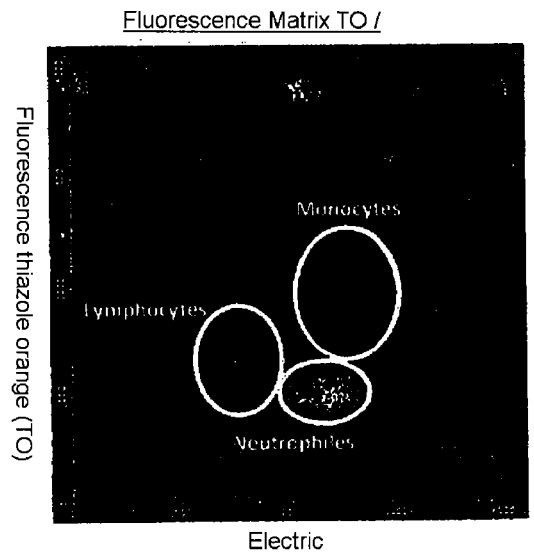

FIGS. 9 to 11 show examples of results obtained with the inspection module 8 of the device described in FIG. 7. In these examples, the blood sample has previously been incubated with a reagent containing Thiazole Orange, which has the particular feature of fluorescing when it is bound to nucleic acid molecules contained in the nucleated cells. The fluorescence is detectable by exciting the Thiazole Orange in the blue range and measuring the fluorescence emitted in the green range.

Here, since the light beam of the illumination unit is filtered in the blue range, the detected signals comprise a first component of large-angle diffraction in the blue range and a second component of fluorescence originating from the Thiazole Orange (excitation in the blue range and emission in the green range).

The measurements obtained are shown in the form of bi-parametric representations in FIGS. 9 to 11. These data allow the different leukocyte populations to be characterised and counted and the presence of nucleic acids contained in the cells to be demonstrated.

Although the average power of this light source is low, the results obtained are very conclusive, the image of FIGS. 9 to 11 indicating good separation of the different leukocyte populations. This is due to a sufficient peak power in the visible range, to an increase in the signal-to-noise ratio, and to optimisation of the optical system.

The embodiment just described is therefore characterised by the use of a white laser as the illumination source, of a light guide in the illumination unit, and the control both of the illumination unit and of the analysis unit by the controller.

It should be noted that those elements are not all indispensable. Thus, it would be possible to control only the illumination unit. Furthermore, as has been mentioned above, the light guide can be omitted or replaced by other elements.

In addition, the white laser described here is a Q-switched source. However, other supercontinuum sources may be used, based on continuous lasers, other (passively and/or actively) Q-switched lasers, or mode-synchronised lasers with and without a time slicer.

The invention is applicable in particular to sources that operate with a pulsed regime because they use moderate average powers (less than 10 W) with high peak powers (greater than 1 kW).

Mode-locked lasers are characterised by a high repetition frequency, greater than 1 MHz, which corresponds to the to-and-fro frequency of the light in the cavity.

The energy carried by those pulses is generally low owing to the duration of the pulses, which is approximately a picosecond and a femtosecond. This type of laser can be used directly by illuminating, with a high recurrence frequency, the cells passing in front of an analysis window.

Under those conditions, a plurality of pulses illuminate a cell and no synchronisation between the optical signal and the biological element is necessary. Nevertheless, it is possible to envisage within the context of this invention the use of an electro-optical modulator (such as a Pockels cell or an acousto-optical modulator) allowing a single pulse to be taken on command, which pulse can be synchronous with moving a cell.

The timing jitter is of the order of several nanoseconds, generally from 1 to 5 ns, and corresponds to the uncertainty of the arrival of the pulse at the biological cell.

This type of system is equivalent to a Q-switched laser but with different characteristics: pulse duration of the order of a picosecond, energy less than 1 μJ, recurrence frequency linked to the modulator varying from approximately 1 kHz to several hundred kHz. This approach is at present not very competitive because the price of such a laser is very high as compared with a Q-switched solid-state laser (diode-pumped YAG:Nd microlaser type). The latter allow pulses of several nanoseconds or picoseconds to be produced in a very simple manner. The principle is based on the rapid modification of the Q-factor of the laser cavity (Q-switch), by acting on the losses or the gain present in the laser cavity. There are two types of Q-switching, active Q-switching and passive Q-switching.

Active Q-switching is based on the introduction of an opto-electronic component into the cavity or on a modulation of the emission of the pump source at the origin of the population inversion.

In the first case, the use of an optoelectronic component allows an emission with a low timing jitter, less than 100 ns, to be obtained. However, this is accompanied by an increase in the length of the laser cavity owing to the insertion of the modulator. The result is the appearance of several longitudinal modes, which can introduce an amplitude instability by beating. The use of a selective filter in the cavity allows this problem to be solved, in return for an increase in the cost of the laser system.

In the second case, rapid modulation of the pumping of the laser also allows pulses of short duration to be obtained. Nevertheless, the fluorescence time of the amplifying medium introduces a time delay and a dispersion in time of the energy at the origin of the Q-switching of the cavity.

The result is a timing jitter greater than 1 μs. Much smaller jitters have nevertheless been obtained in cases where the laser source has a microscopic cavity, for example diode lasers or microlasers. However, these jitter-free sources require amplification in order to permit a spectral extension by non-linear effect. The complexity and the cost of such a system are generally high.

Passive laser Q-switching is based on the introduction of an optical component of the saturable absorbent type into the laser cavity. No external power source is necessary for Q-switching this "time gate": merely the amplified spontaneous emission of the laser permits saturation of its absorption and therefore a rapid modification of the quality coefficient of the cavity.

The resulting small space requirement allows very short resonators to be produced, which permits the production of pulses of between several tens of picoseconds and several nanoseconds.

This type of source generally has a jitter greater than 1 μs, and synchronisation thereof by external control is difficult. The cost of these sources is low, and the pulses obtained are generally shorter than those obtained by active Q-switching.

Q-switching that is both active and passive allows the advantages of the two methods to be combined. Active Q-switching allows the output pulse to be synchronised with another system or a biological element, while the passive Q-switcher allows short pulses to be obtained. The timing jitters are of the order of a few microseconds for recurrence frequencies of between 1 and 10 kHz.

There also exist systems with double active and passive Q-switching, that is to say two active Q-switchings and one passive Q-switching or two passive Q-switchings and one active Q-switching. These lasers use the combination of each effect to improve the performances of the sources in terms of timing jitter and pulse duration.

Within the context of the invention, any laser source that uses at least one extra- or intra-cavity active Q-switching system can be used for the intended applications, provided that the timing jitter is less than about 3 μs.

In order to use supercontinua in flow cytometry, it is necessary for the lasers to have specific characteristics. Firstly, the pulse creation delay (PCD) must be constant. That delay corresponds to the time offset between the Q-switching signal sent to the supercontinuum laser and the creation of the light pulse that follows.

Secondly, the jitter is the maximum time variation between two times at which the light pulse appears. In order for measurements to be reliable in flow cytometry with a supercontinuum, the variation of the PCD and of the jitter must preferably be less than more or less 1 μs. Finally, the energy variation between the light pulses over the frequency range must be less than 5%.

An important element is that all the sources can be controlled by the controller, either pulse by pulse when they are Q-switched, or, for example, by the use of an acousto-optical modulator which acts as a switch which is able to select one or more pulses. It can be an MOEMS or en electro-optical element of the Pockels type.

Other illumination sources can also be used, such as diodes, laser diodes, or a plurality of monochromatic lasers connected to an acousto-optical modulator controlled by the controller.

In addition, it would be possible to add other optical inspection modules further downstream in the vessel, in order to carry out other measurements. Such inspection modules may likewise be controlled by the controller 6, in a manner similar to that effected for the control of the second inspection module 8. In that case, it will be necessary to provide other signal generators in the controller 6.

Q-switching of several sources in cascade may also be carried out by managing the delay(s) between each source.

The invention claimed is:

1. A device for inspecting a biological fluid, comprising:
a channel through which the fluid flows;
a first inspection module arranged in a first region of the channel; and
a second inspection module arranged in a second region of the channel, wherein the device is configured to provide a quantity that is representative of an output of the second inspection module,
wherein the first inspection module is configured to measure at least one electrical property of the fluid passing through the first region, the second inspection module is configured to measure at least one optical property of the fluid passing through the second region, and
the inspection device further comprises a controller connected to the first inspection module and to the second inspection module and configured to control the second inspection module according to an output of the first inspection module,
wherein the controller is configured to emit a control signal having a delay chosen relative to an output signal of the first inspection module, wherein the controller is configured to define the chosen delay as a function of distance between the first region and the second region, of at least one time property of the second inspection module, and of a speed of the fluid passing through the channel.

2. A device according to claim 1, wherein the second inspection module comprises an illumination unit configured to illuminate the second region, and an analysis unit configured to collect and measure at least one optical property of a light that has passed through the second region, and wherein the controller controls the illumination unit.

3. A device according to claim 2, wherein the controller further controls the analysis unit.

4. A device according to claim 2, wherein the illumination unit comprises an illumination source comprising at least one laser and/or at least one light-emitting diode and/or at least one laser diode.

5. A device according to claim 4, wherein the illumination source comprises a white laser.

6. A device according to claim 4, wherein the illumination source comprises a plurality of lasers each having a respective emission wavelength.

7. A device according to claim 4, wherein the illumination unit comprises a light guide comprising a first end for receiving a light emitted by the illumination source, and a second end for illuminating the second region.

8. A device according to claim 4, wherein the illumination unit comprises an acousto-optical modulator configured to receive the light emitted by the illumination source and to re-emit it selectively under control of the controller.

9. A device according to claim 1, comprising one or more auxiliary inspection modules arranged in respective regions of the channel, each configured to measure at least one optical property of the fluid passing through its respective region, and wherein the controller is configured to control at least some of the auxiliary inspection modules.

* * * * *